(12) United States Patent
Wang et al.

(10) Patent No.: US 12,119,117 B2
(45) Date of Patent: Oct. 15, 2024

(54) METHOD AND SYSTEM FOR DISEASE QUANTIFICATION OF ANATOMICAL STRUCTURES

(71) Applicant: SHENZHEN KEYA MEDICAL TECHNOLOGY CORPORATION, Shenzhen (CN)

(72) Inventors: Xin Wang, Seattle, WA (US); Youbing Yin, Kenmore, WA (US); Bin Kong, Charlotte, NC (US); Yi Lu, Seattle, WA (US); Hao-Yu Yang, Seattle, WA (US); Xinyu Guo, Redmond, WA (US); Qi Song, Seattle, WA (US)

(73) Assignee: SHENZHEN KEYA MEDICAL TECHNOLOGY CORPORATION, Shenzhen (CN)

( * ) Notice: Subject to any disclaimer, the term of this patent is extended or adjusted under 35 U.S.C. 154(b) by 420 days.

(21) Appl. No.: 17/726,307

(22) Filed: Apr. 21, 2022

(65) Prior Publication Data
US 2022/0351863 A1 Nov. 3, 2022

Related U.S. Application Data

(60) Provisional application No. 63/178,940, filed on Apr. 23, 2021.

(51) Int. Cl.
*G16H 50/30* (2018.01)
*G06N 3/045* (2023.01)
(Continued)

(52) U.S. Cl.
CPC .............. *G16H 50/30* (2018.01); *G06N 3/045* (2023.01); *G06T 7/0012* (2013.01); *G06V 10/42* (2022.01);
(Continued)

(58) Field of Classification Search
None
See application file for complete search history.

(56) References Cited

U.S. PATENT DOCUMENTS

8,913,818 B2 * 12/2014 Lang .................... A61B 6/4423
382/132
9,155,501 B2 * 10/2015 Lang .................... A61B 5/4509
(Continued)

*Primary Examiner* — Anand P Bhatnagar
(74) *Attorney, Agent, or Firm* — Bayes PLLC (57) ABSTRACT

This disclosure discloses a method and system for predicting disease quantification parameters for an anatomical structure. The method includes extracting a centerline structure based on a medical image. The method further includes predicting the disease quantification parameter for each sampling point on the extracted centerline structure by using a GNN, with each node corresponds to a sampling point on the extracted centerline structure and each edge corresponds to a spatial constraint relationship between the sampling points. For each node, a local feature is extracted based on the image patch for the corresponding sampling point by using a local feature encoder, and a global feature is extracted by using a global feature encoder based on a set of image patches for a set of sampling points, which include the corresponding sampling point and have a spatial constraint relationship defined by the centerline structure. Then, an embed feature is obtained based on both the local feature and the global feature and input into to the node. The method is able to integrate local and global consideration factors of the sampling points into the GNN to improve the prediction accuracy.

20 Claims, 8 Drawing Sheets

(51) Int. Cl.
*G06T 7/00* (2017.01)
*G06V 10/42* (2022.01)
*G06V 10/44* (2022.01)
*G06V 10/82* (2022.01)
*G16H 30/40* (2018.01)

(52) U.S. Cl.
CPC .............. *G06V 10/44* (2022.01); *G06V 10/82* (2022.01); *G16H 30/40* (2018.01)

(56) References Cited

U.S. PATENT DOCUMENTS

| | | | |
|---|---|---|---|
| 9,275,469 B2 * | 3/2016 | Lang | G06T 7/0012 |
| 9,767,551 B2 * | 9/2017 | Lang | G06T 7/0012 |
| 11,462,326 B2 * | 10/2022 | Wang | G06N 3/082 |
| 11,705,226 B2 * | 7/2023 | Colley | G16H 50/70 |
| | | | 705/3 |
| 11,823,432 B2 * | 11/2023 | Li | G06V 10/454 |
| 2015/0193944 A1 * | 7/2015 | Lang | A61B 6/505 |
| | | | 382/132 |
| 2016/0253797 A1 * | 9/2016 | Lang | G09B 23/30 |
| | | | 382/132 |
| 2020/0402666 A1 * | 12/2020 | Wang | G06N 3/084 |
| 2021/0090694 A1 * | 3/2021 | Colley | G16H 15/00 |
| 2022/0415510 A1 * | 12/2022 | Wang | G16H 50/20 |

\* cited by examiner

METHOD AND SYSTEM FOR DISEASE QUANTIFICATION OF ANATOMICAL STRUCTURES

CROSS REFERENCE TO RELATED APPLICATION

This application is based on and claims the priority of U.S. Provisional Application No. 63/178,940, filed Apr. 23, 2021, which is incorporated herein by reference in its entirety.

TECHNICAL FIELD

This disclosure relates to a field of anatomical structure analysis using artificial intelligence, especially relates to a method and system for predicting disease quantification parameters for an anatomical structure.

BACKGROUND

Accurate disease quantification parameters for an anatomical structure facilitate accurate diagnosis. For example, it has been proved that fractional flow reserve (FFR) is a reliable index for the assessment of cardiac ischemic. FFR can be measured with a pressure wire, but this procedure is invasive and only one or a few values are measured throughout the vascular tree. Attempts have been made to estimate FFR using learning-based methods. This learning-based FFR estimation is basically a low-data problem, because only one, few, or several locations are provided with ground authenticity measurements. Since only a small amount of invasive FFR values (measured by pressure wire) are available for the training process, it is very challenging to provide accurate predictions for the entire coronary artery tree. The existing machine learning-based methods require simulated FFR values as the ground truth of training models. However, the simulated FFR values are usually calculated by numeric flow simulation-based methods, which are time-consuming and inaccurate for training machine learning models. Therefore, the performance of machine learning-based methods is highly restricted by simulation methods, which makes the prediction performance of the machine learning-based methods poor, and the prediction accuracy of disease quantitative parameters for an anatomical structure low.

SUMMARY

The embodiments of this disclosure provide a method of predicting disease quantification parameters for an anatomical structure, which can seamlessly integrate the information of sampling points from the centerline structure in the whole anatomical structure, and integrate local consideration factors and global consideration factors of sampling points into a Graph neural network (GNN), so as to accurately predict disease quantitative parameters for an anatomical structure only by using limited label data.

In order to solve the above technical problems, the embodiments of this disclosure adopt the following technical solutions.

According to a first aspect of this disclosure, a method of predicting disease quantification parameters for an anatomical structure is provided. The method may include receiving a medical image containing the anatomical structure. The method may include extracting a centerline structure based on the medical image. The method may include predicting the disease quantification parameter for each sampling point on the extracted centerline structure by using a Graph neural network (GNN) where each node of the GNN corresponds to a sampling point on the extracted centerline structure and each edge of the GNN corresponds to a spatial constraint relationship between two sampling points. For each node of the GNN, a local feature may be extracted based on an image patch for the corresponding sampling point by using a local feature encoder and a global feature may be also extracted by using a global feature encoder based on a set of image patches for a set of sampling points. The set of sampling points may include the corresponding sampling points and have a spatial constraint relationship defined by the centerline structure. Then an embed feature may be obtained based on both the local feature and the global feature and input into the node of the GNN.

According to a second aspect of this disclosure, a system for predicting disease quantification parameters for an anatomical structure is provided. The system may include an interface and a processor. The interface may be configured to receive a medical image containing the anatomical structure. The processor may be configured to extract a centerline structure based on the medical image and predict the disease quantification parameter for each sampling point on the extracted centerline structure by using a Graph neural network (GNN) where each node of the GNN corresponds to a sampling point on the extracted centerline structure and each edge of the GNN corresponds to a spatial constraint relationship between two sampling points. For each node of the GNN, a local feature may be extracted based on an image patch for the corresponding sampling point by using a local feature encoder and a global feature may be also extracted by using a global feature encoder based on a set of image patches for a set of sampling points. The set of sampling points may include the corresponding sampling points and have a spatial constraint relationship defined by the centerline structure. Then an embed feature may be obtained based on both the local feature and the global feature and input into the node of the GNN.

According to a third aspect of this disclosure, this disclosure provides a non-transitory computer-readable storage medium on which computer-executable instructions are stored. The computer-executable instructions, when executed by the processor, may implement the method of predicting disease quantification parameters for an anatomical structure according to various embodiments of this disclosure. The method may include receiving a medical image containing the anatomical structure. The method may include extracting a centerline structure based on the medical image. The method may include predicting the disease quantification parameter for each sampling point on the extracted centerline structure by using a Graph neural network (GNN) where each node of the GNN corresponds to a sampling point on the extracted centerline structure and each edge of the GNN corresponds to a spatial constraint relationship between two sampling points. For each node of the GNN, a local feature may be extracted based on an image patch for the corresponding sampling point by using a local feature encoder and a global feature may be also extracted by using a global feature encoder based on a set of image patches for a set of sampling points. The set of sampling points may include the corresponding sampling points and have a spatial constraint relationship defined by the centerline structure. Then an embed feature may be obtained based on both the local feature and the global feature and input into the node of the GNN.

By extracting local features of the sampling points on the centerline structure, and extracting global features based on a set of sampling points, and obtaining the embed features for input into the GNN using both the local features and global features, the disclosed methods can seamlessly integrate the information of sampling points from the centerline structure in the whole anatomical structure, and integrate local consideration factors and global consideration factors of sampling points into GNN, so as to accurately predict disease quantitative parameters for an anatomical structure only by using limited labeled data.

DETAILED DESCRIPTION

In order to have a better understanding of this disclosure for those skilled in the art, the embodiments of this disclosure are described in detail as follows according to the attached drawings, which, however, does not limit the present invention.

Figure 1A:
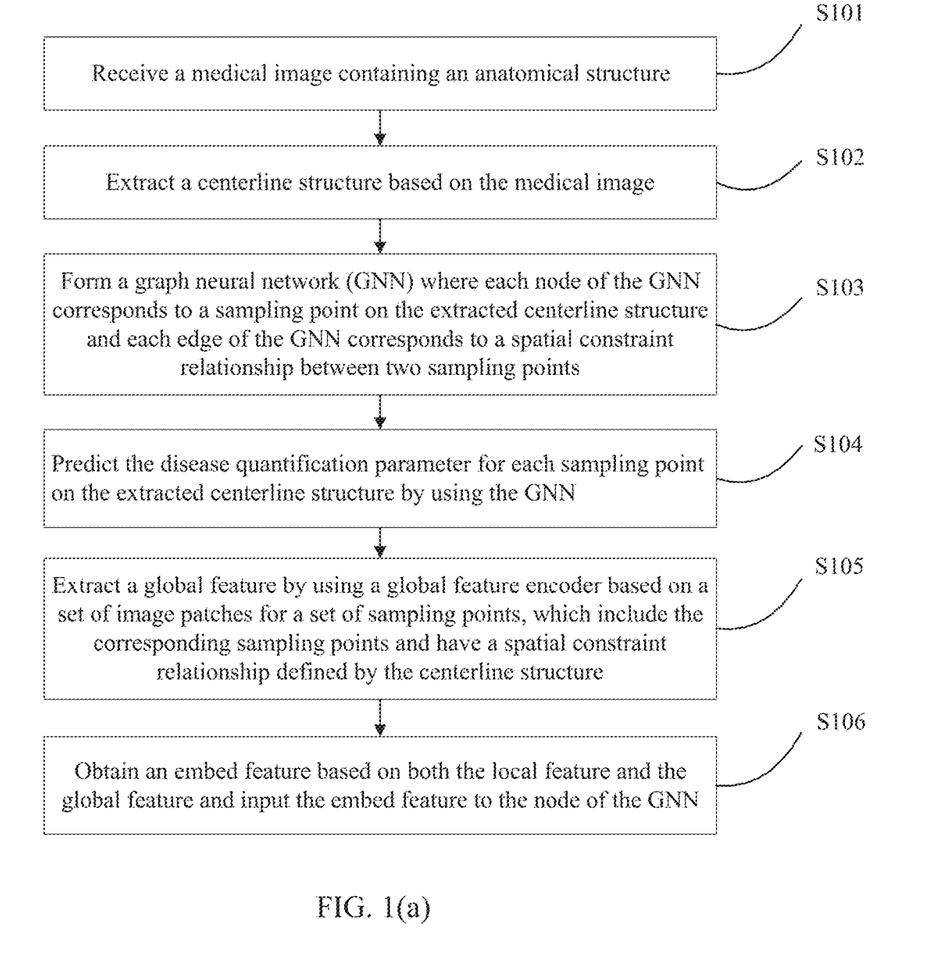
FIG. 1(a) illustrates a flowchart of a method of predicting disease quantification parameters for an anatomical structure, according to an embodiment of this disclosure.

A method of predicting disease quantification parameters for an anatomical structure is provided in this disclosure. FIG. 1 (a) shows a flowchart of a method of predicting disease quantification parameters for an anatomical structure, according to an embodiment of this disclosure. As shown in FIG. 1 (a), the method starts with step S101: receive a medical image containing an anatomical structure.

It shall be acknowledged that the term "anatomical structure" herein may refer to blood vessels, airways with a tree structure, etc., but this disclosure is not limited thereto. A medical image may be a complete image or an image patch cropped from a complete image, and may be in two-dimensional (2D) or three-dimensional (3D) form. It can be understood that a medical image may be acquired by using various medical equipment, such as CT image, MRI image, ultrasound image, etc., such as MRI image containing blood vessels, Mill image of brain structure, etc.

At S102, a centerline structure may be extracted based on the medical image.

In some embodiments, a neural network may be utilized to extract the centerline structure. Neural network algorithm is an algorithm mathematical model that imitates the behavior of brain neural network and performs distributed parallel information processing. Such kind of network depends on the complexity of the system and achieves the purpose of processing information by adjusting the mutual coupling relationship between the internal neurons. The centerline structure of the anatomical structure may be extracted quickly and accurately by performing process on the obtained medical images containing the anatomical structure using the trained neural network.

In some embodiments, a neural network may be used to segment a medical image containing an anatomical structure, so as to extract the centerline structure. Then, the centerline structure may be sampled to obtain sampling points. For example, the sampling points may be the positions where the disease quantitative parameters are of interest. As another example, a set of points can be selected among the points distributed along the blood vessel as sampling points, so as to obtain the embed features and further predict the distribution profile of the disease quantitative parameters (such as FFR) of the blood vessels.

Then, features may be extracted from these sample points as vertices (nodes) of the graph, so as to create a graph representation. Particularly, these features may be disease-related features.

In some embodiments, the segmentation of the centerline structure for an anatomy structure may be performed automatically, semi-automatically or manually. Second, points on the centerline are sampled as vertices (V) of the graph (G). For each sampling point on the centerline, feature information (for example, may be referred to as a local feature map) may be extracted based on the image patch (or mask patch) at each sampling point. For a set of sampling points on the centerline, feature information (for example, it can be referred to as a global feature map) may also be extracted based on a set of image patches at the corresponding set of sampling points. The following detailed description is mainly based on this situation. However, it should be noted that the basis of feature information extraction s not limited to image patches at each (set of) sampling point (s), and may also include various defined disease-related features at each (set) sampling point. Specifically, disease-related features may include, but are not limited to, structural features, intensity features, and/or other derived features, and the like. As examples of structural features, geometric features may include any type of radius, area, stenosis; volume, length, curvature, and the like. Intensity features may include any type of intensity elated measures, such as intensity statistic measurements (minimum, maximum, average, etc.). The other derived features may be any feature derived based on tree structure, strength, or even information related to other anatomic structures. In some embodiments, the disease-related feature may also include pressure drops or resistance estimated using simplified equations. As input, other channels may be stacked to represent various disease-related features, such as but not limited to geometric feature information, intensity feature information, blood feature information, etc.

The points on a centerline structure may be linked by edges, which may be undirected. In some embodiments, edges may also be directed. Particularly, an undirected edge may be treated as two directed edges, indicating that there is a relationship or association between two nodes. In general, directed edges may carry more information than undirected edges.

In some embodiments, the information may propagate from the root to the tip of the anatomy structure, and it may also propagate in the opposite direction (e.g., from the tip to the root of the tree). In other words, information propagation or transfer between nodes of an anatomy structure may be achieved by considering both directions.

According to this disclosure, taking the anatomical structure as a vessel tree structure as an example, the tree T is associated with the graph $GT=(V, E)$, where the nodes $vi \in V$ correspond to the feature vectors or embedding of points on the centerline structure (both with ground truth and unknown values), and edges $ei \in E$ correspond to the directed or undirected edges between the points. According to the present disclosure, both implicit representations (i.e., feature embedding) and explicit relationships (i.e., graph) are fused to learn the disease prediction model for the entire anatomy.

At S103, a Graph neural network (GNN) is formed, where each node of the GNN corresponds to a sampling point on the extracted centerline structure and each edge of the GNN corresponds to a spatial constraint relationship between the sampling points. The GNN constructed in this way may transfer information (message passing) between nodes with ground truth and nodes without ground truth through training learning, and may obtain a deep memory graph neural network with good training effect even in the absence of label data.

Specifically, each node of the (INN is set as corresponding to a sampling point out of centerline structure, and each edge of the GNN corresponds to the spatial constraint relationship between the sampling points. The spatial constraint relationship between the sampling points may reflect the relative relationship between the sampling points, for example, the information transfer direction between the sampling points. Each edge of the (INN is set to correspond to the spatial constraint relationship between the sampling points, so that GNN may consider the relative relationship between sampling points when predicting disease quantification parameters for an anatomical structure, thereby obtaining more accurate prediction results. It is contemplated that a (INN does not have to be physically formed and stored as a graph as a whole. Instead, a GNN may be formed by merely the identification of the nodes and edges and the nodes and edges may be stored.

At S104, the disease quantification parameter may be predicted for each sampling point on the extracted centerline structure by using the GNN as follows. Particularly, for each node of the GIN N, a local feature may be extracted based on an image patch for the corresponding sampling point by using a local feature encoder.

At S105, a global feature may be extracted by using a global feature encoder based on a set of image patches for a set of sampling points, which include the corresponding sampling point and have a spatial constraint relationship defined by the centerline structure.

Particularly, 2D/3D image patches may be extracted for each sampling point on the centerline structure. Then, the local feature corresponding to each sampling point may be extracted by using a local feature encoder, and the local feature may reflect the local disease-related feature information of the sampling point.

For a set of sampling points, it has a spatial constraint relationship defined by the centerline structure, and the spatial constraint relationship may reflect the relative relationship between each sampling point in the set and may reflect the overall feature information of the whole set of sampling points. For example, the overall feature information may include the overall information transmission direction of the set of sampling points, the change trend of feature information, and the like. In S105, global features are extracted for a set of image patches for a set of sampling points, and the overall feature information of each set of sampling points may be obtained.

In some embodiments, the global feature encoder and the local feature encoder may be the same encoder or different encoders, as long as the local features of the corresponding sampling points and the global features of a set of sampling points may be obtained, which is not specifically limited by this disclosure.

At S106, an embed feature may be obtained based on both the local feature and the global feature and input into to the corresponding node of the GNN. Particularly, the embed feature is obtained by using the local features that may reflect the disease-related local features of each sampling point itself and the global features that may reflect the overall feature information of a whole set of sampling points, and then the embed feature is input into the GNN to predict disease quantification parameters for anatomy structure. In this way, in the process of using GNN to predict the disease quantitative parameters for an anatomical structure, not only the local feature of each sampling point itself, but also the overall feature of a set of sampling points are considered, and it also effectively utilizes the learning ability of GNN to transfer information between nodes with ground truth and nodes without ground truth, so that higher accuracy prediction results may be achieved.

It should be noted that FFR is a reliable indicator for evaluating cardiac ischemia, and the embodiments in this disclosure are described by taking prediction of FFR as an example, but this disclosure is not limited thereto. Rather, this disclosure is applicable to any disease quantification parameter for any anatomical structure.

Taking the prediction of FFR as an example, the medical image may be a medical image containing blood vessels, and the anatomical structure is a blood vessel tree structure. The centerline structure of the vessel tree may be extracted based on the medical image containing the vessel.

In some embodiments, for medical images containing blood vessels, initial artery, segmentation with centerline structure may be performed automatically, semi-automatically, or manually. For each sampling point on the centerline structure, disease-related features may be extracted, which may include, but are not limited to, structural features, intensity features, and/or other derived features, and the like. For predicting FFR, these disease-related features might be blood pressure drop or resistance estimated using a simplified equation, etc.

Then, after the centerline structure of the vessel tree is extracted, a Graph neural network (GNN) is constructed, so that each node of the GNN corresponds to the sampling point on the extracted centerline structure of the vessel tree, and each edge of the GNN corresponds to the spatial constraint relationship between sampling points. The input of each node in the GNN may be a 2D/3D image patch of the corresponding sampling point of the centerline structure, and the output of each node is the disease quantification parameter of the blood vessel. Additionally, the method may include obtaining label data of a set of nodes, and the number of nodes in the set of nodes is less than the total number of nodes in the GNN. Furthermore, the method may further include training the GNN by transferring information between the set of nodes and other nodes based on the label data of the set of nodes.

Based on a set of image patches for a set of sampling points, the global feature may be extracted by using a global feature encoder. The embed feature may be obtained based on both the local feature and the global feature, and then input into the corresponding respective node of the GNN. In this manner, the GNN may be utilized to predict FFR distribution profile at a sequence of sampling points.

In some embodiments, the GNN may include a graph convolutional neural network (GCN). The goal of GCN is to generalize convolutional neural network architectures to non-Euclidean domains (such as graphs). Specifically, the graph convolution may define convolution directly on the graph, so that for each node, a series of convolution operations may be performed using a graph convolution layer and considering its spatially close neighbors. In this way, not only the local hidden information to the node may be extracted, but also the physical constraint relationship in the non-Euclidean domain between the node and the surrounding nodes may be embed, so that it makes the training results in the absence of ground truth better and the prediction results more accurate.

The method of predicting disease quantification parameters for an anatomical structure provided by this disclosure extracts the local features of the sampling points of the center line and also the global features based on a set of sampling points, and obtains embed features for input into GNN based on both local features and global features, enabling seamless integration of information from sampled points of centerline structures throughout the anatomy, structure. By incorporating both local and global consideration factors of sampled points and inputting into the GNN, it may predict accurately the disease quantitative parameters for the anatomical structure only by using limited label data.

In some embodiments, each of the local feature encoder and the global feature encoder may employ a two-level attention mechanism by utilizing a first-level attention module and a second-level attention module. The first level attention module is configured to extract the lesion location-aware attention map, while the second-level attention module is configured to extract the pixel-to-pixel inter-dependence attention map.

It can be understood that the attention mechanism may consider the degree of neighbor nodes (also known as neighbors) and edge information such as attention weights, integrate the relationship among each piece of information, and allow the model to dynamically, pay attention to specific parts of the input, thus complete the current task more efficiently. A dual-level attention mechanism is constructed using the first-level attention module for extracting the lesion location-aware attention map and the second-level attention module for extracting the pixel-to-pixel inter-dependence attention map, and the constructed dual-level attention mechanism acts as a local feature encoder and a global feature encoder, so that each encoder not only may take into account the inter-dependence attention relationship between the lesion location of the anatomical structure and the extracted pixels, but also take into account the incidence relation between the lesion position and the inter-dependence attention between the pixels. This enables each encoder to extract richer feature information from image patches at the corresponding sampling points, thereby achieving higher accuracy when using GNN to predict disease quantification parameters for an anatomical structure.

Figure 1B:
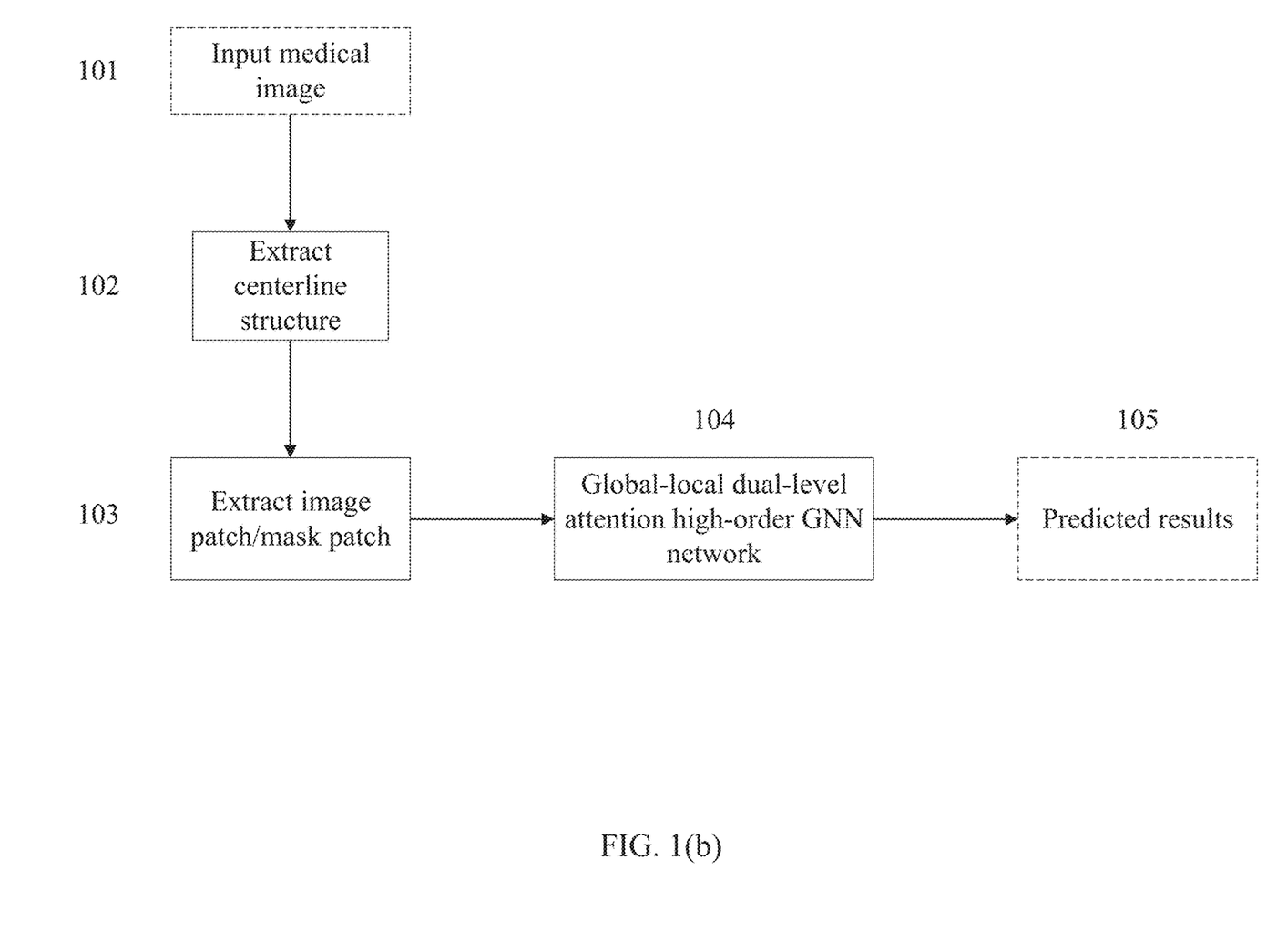
FIG. 1(b) illustrates a framework used by the method of FIG. 1(a), according to an embodiment of this disclosure.

Taking prediction of FFR as an example, the input medical image may be a medical image containing blood vessels, for example, an MIll image containing blood vessels. As shown in FIG. 1(b), a medical image (101) is received as an input. The centerline structure (102) of the blood vessel tree is extracted from the medical image 101, and then image patches/mask patches (103) are extracted for the sampling points on the centerline structure. The extracted image patch/mask patch 103 may be input into the global-local dual-level attention high-order GNN network 104, and the predicted result 105 may be obtained and output. By using the first-level attention module of the global-local dual-level attention high-order GNN network 104, the narrow position-aware attention map of the blood vessel may be extracted. Besides, the second-level attention module may use a non-local network to detect a more accurate pixel-to-pixel inter-dependence attention map. The first-level attention module and the second-level attention module may provide more discriminative feature representations for disease prediction and lesion localization (such as stenosis localization for FFR prediction), resulting in higher accuracy of FFR prediction.

As shown in FIG. 1(b), the GNN may include a high-order GNN. Particularly, in general GNNs, nodes only receive latent representations from their immediate (first-degree) neighbors, while the high-order GNN uses higher-order message passing, where nodes receive latent representations from both their immediate (first-degree) neighbors and from further N-degree neighbors at every message passing step. The high-order GNN may take higher-order information into account, and learn from a small number of labeled data points or even a single one labeled data point during training, by means of propagating information from labeled data points to unlabeled data points. This enables more accurate prediction results when predicting disease quantification parameters foe an anatomical structure.

In some embodiments, the anatomical structure may include an anatomical tree structure or an anatomical graph structure. For example, the coronary artery is a tree structure, and the method proposed in this disclosure may be adapted to predict non-invasive functional assessment of fractional flow reserve (FFR) for a coronary artery, or stenosis/lesion detection in the coronary artery, to obtain more accurate prediction results.

Figure 2A:
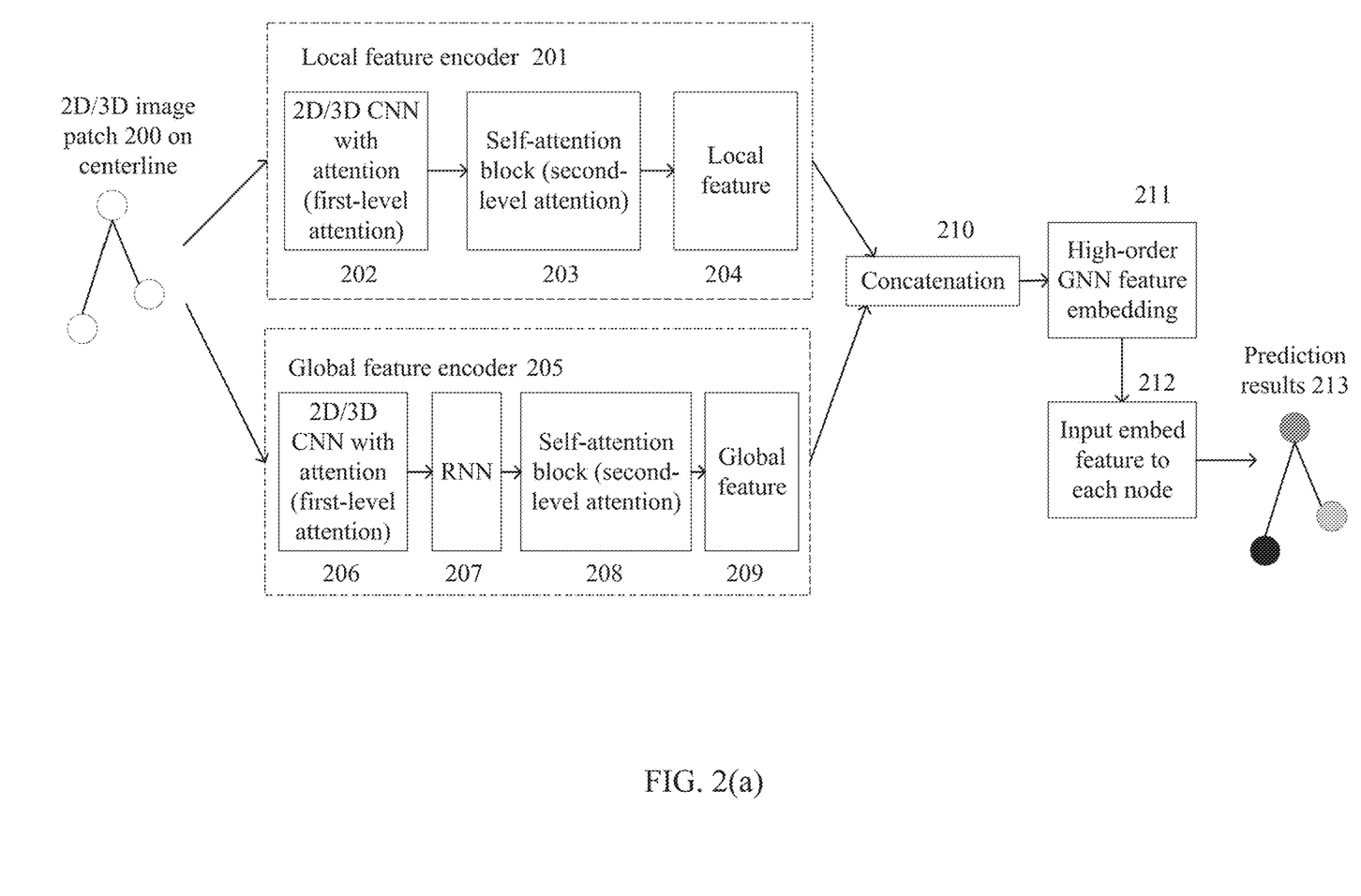
FIG. 2(a) illustrates a framework implemented by an exemplary method for predicting disease quantification parameters for an anatomical structure, according to an embodiment of this disclosure.

In some embodiments, the local feature encoder may include a first convolutional neural network (CNN) incorporating an attention mechanism for localization and a first self-attention block following it. The first self-attention block may incorporate an attention mechanism with pixel-to-pixel correlation. FIG. 2(a) shows a flowchart of a method for predicting disease quantification parameters for an anatomical structure according to a specific embodiment of this disclosure. As shown in FIG. 2(a), for the 2D/3D image patch 200 on the centerline, a local feature encoder 201 is used to obtain the local feature 204. Particularly, a CNN incorporating an attention mechanism for localization, i.e., the 2D/3D CNN with attention (first-level attention) 202 in FIG. 2(a), is combined with the first self-attention block, i.e., the self-attention block 203 (second-level attention) in FIG. 2(a). And the local feature 204 may be output by the first self-attention block incorporating an attention mechanism with pixel-to-pixel correlation, i.e., the self-attention block 203 (second-level attention) in FIG. 2(a).

FIG. 2 (b) shows an embodiment where the local feature 204 is obtained by means of using a local feature encoder 201 based on the 2D/3D image patch 200 on the centerline. For example, the local feature encoder 201 may include a 2D/3D CNN with first-level attention 202 and a self-attention block 203 in sequence.

In some embodiments, the first convolutional neural network (CNN) may be any 2D/3D CNN network, such as VGG, ResNet, etc. It can be understood that the first convolutional neural network may be any attention mechanism for localization, such as residual attention, and the first self-attention block may be any pixel-to-pixel correlation method, such as a nonlocal network, etc., which are not specifically limited herein.

In some embodiments, the global feature encoder may include a second convolutional neural network (CNN) incorporating an attention mechanism for localization, followed by a recurrent neural network (RNN), and then a second self-attention block incorporating an attention mechanism with inter-pixel correlation. The RNN is configured to accumulate information from the root of the anatomical structure to the current sampling point. As an example, as shown in FIG. 2(a), for the global feature encoder 205, a 2D/3D CNN with attention (first-level attention) 206 is combined with the RNN 207, and then the output of the RNN 207 is transferred to the self-attention block 208 (second-level attention), by which the global feature 209 is extracted. As an example, RNN 207 is widely applicable to sequence learning tasks because of its ability to capture long-term and short-term information. Therefore, RNN 207 is employed to learn global features, such as in the FFR prediction problem, where RNN 207 is configured to accumulate information from the root of the coronary artery vessel to the current point. In this manner, the global feature of the centerline structure may be improved, so that the disease quantification parameters for the anatomical structure predicted based on the obtained global features have a higher accuracy. FIG. 2(c) illustrates an embodiment where the global feature encoder 205 is utilized to obtain the global feature 209 based on the 2D/3D image patch 200 on the centerline. For example, the global feature encoder 205 may include a 2D/3D CNN with first-level attention 206, an RNN 207, and a self-attention block 208 in sequence.

Figure 2B:
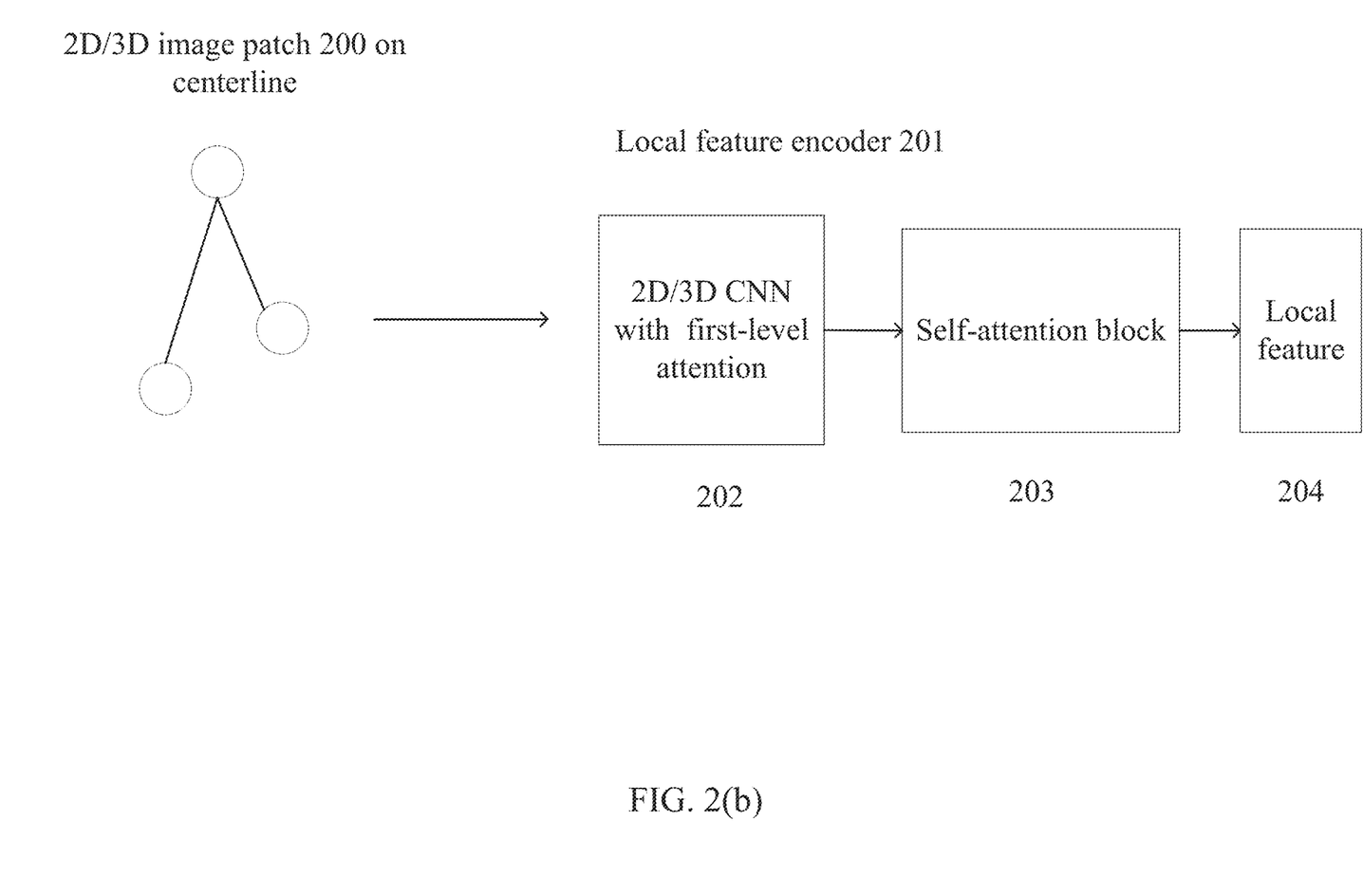
FIG. 2(b) illustrates a framework implemented by an exemplary method of local feature learning, according to an embodiment of this disclosure.
Figure 2C:
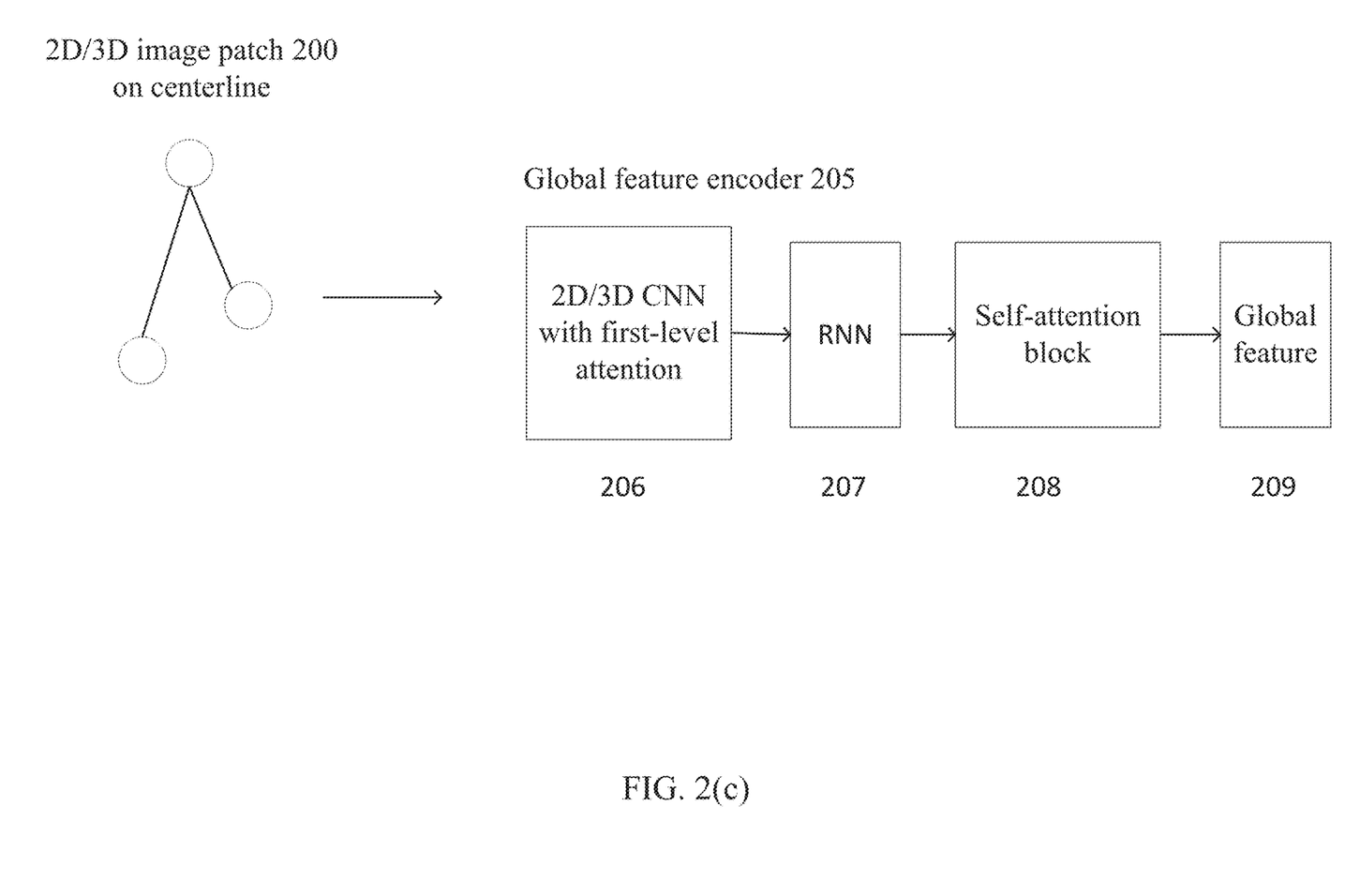
FIG. 2(c) illustrates a framework implemented by an exemplary method of global feature learning according to an embodiment of this disclosure.
Figure 2D:
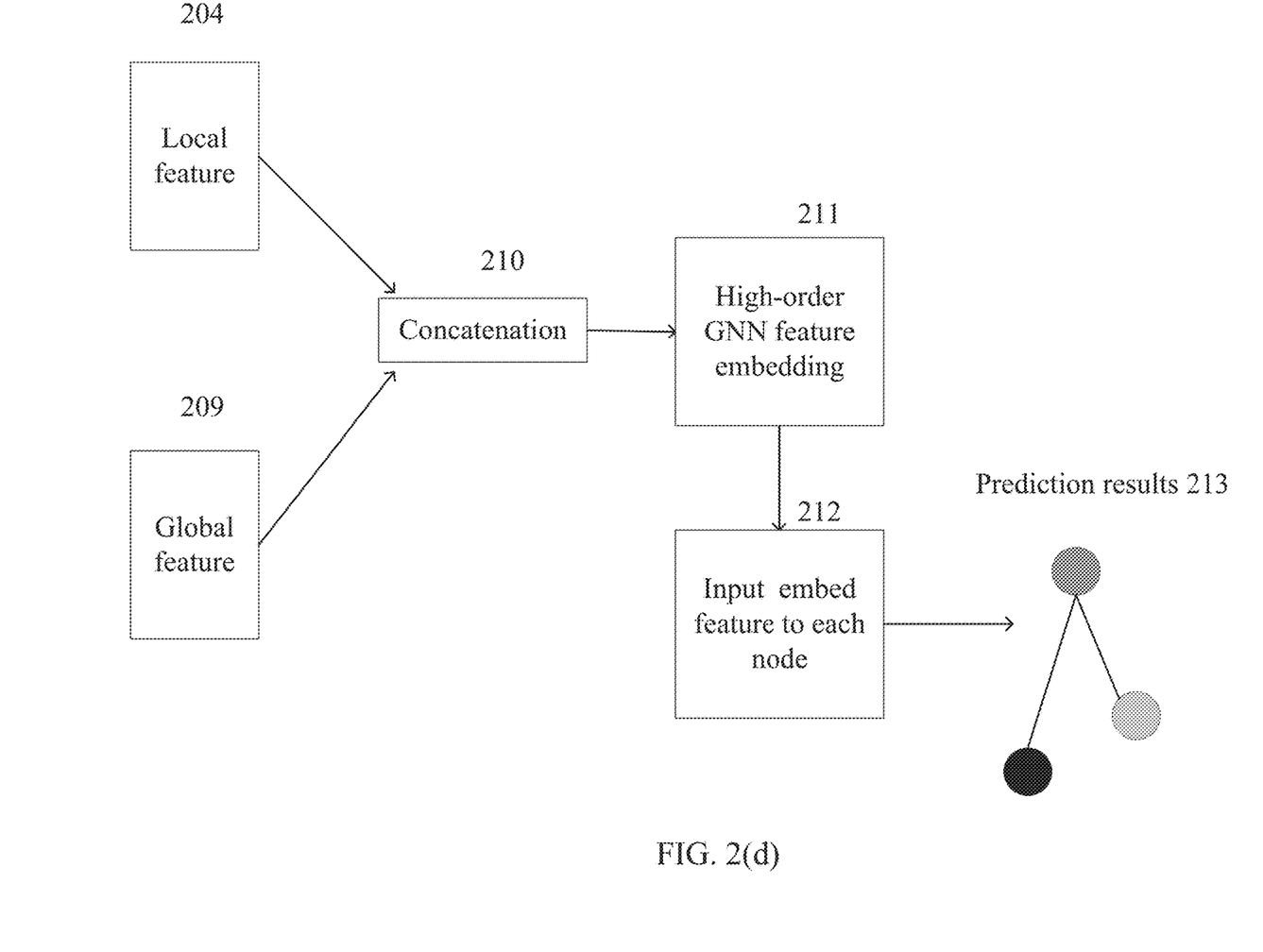
FIG. 2(d) illustrates a framework implemented by an exemplary method of predicting disease quantification parameters for an anatomical structure using local features and global features, according to an embodiment of this disclosure.

As shown in FIG. 2(d), after obtaining the local feature 204 obtained as shown in FIG. 2(b) and the global feature 209 obtained as shown in FIG. 2(c), the local feature 204 and the global feature 209 may be concatenated (concatenation 210 as shown in FIG. 2(d)), so as to obtain the embed feature. Then high-order GNN feature embedding 211 may be performed, and the embed features may be input to each node 212, so as to obtain the prediction result 213 of the disease quantification parameters for the anatomy structure.

In some embodiments, the second convolutional neural network CNN may be any 2D/3D CNN network, such as VGG, ResNet, etc. The second convolutional neural network may be any attention mechanism used for localization, such as residual attention. RNN may use any RNN unit, such as LSTM, GRU, convLSTM, convGRU, etc. The second self-attention block may be any pixel-to-pixel correlation method, such as a nonlocal network, etc. This disclosure does not specifically limit the frame of the second convolutional neural network CNN or the RNN.

It is understandable that the attention mechanisms for localization of the first convolutional neural network and the second convolutional neural network may adopt the same attention mechanism, such as the 2D/3D CNN with attention as shown in FIG. 2(a), and may also adopt different attention mechanisms, which are not specifically limited in this disclosure.

It can be understood that the first self-attention block and the second self-attention block may be the same or different, which is not specifically limited in this disclosure.

In some embodiments, the attention mechanism for localization includes residual attention, and each self-attention block includes a nonlocal network. For predicting FFR, the first-level attention module with residual attention may extract narrow position-aware attention maps, and the self-attention block with nonlocal network may detect more accurate pixel-to-pixel interdependent attention maps, which may provide more discriminative feature representation for the prediction of FFR score value and the prediction of narrow localization, so that the prediction accuracy may be improved.

In some embodiments, obtaining the embed feature based on both the local feature and the global feature may further include concatenating the local feature with the global feature to obtain the embed feature (as shown in FIG. 2(a)). Particularly, the extracted local feature may be expanded into a one-dimensional vector, the extracted global features may be also expanded similarly into a one-dimensional vector, and then the two expanded one-dimensional vectors may be concatenated to obtain the embed features, so that the embed feature contains both the local feature and the global feature therein, and it may obtain more accurate prediction results upon being input into the GNN.

In some embodiments, the GNN includes a graph convolution based neural network or a graph gating based neural network.

For example, graph convolutional neural networks are able to generalize CNN architectures to non-Euclidean domains. The graph convolution can define convolutions directly on the graph, operating on spatially close neighbors. A graph convolutional neural network may be expressed as: $Z=GCN(X, A)$, where $X \in \mathbb{R}^{N \times C}$ is the input, N is the number of nodes, C is the dimension of feature embedding, and A is an adjacent matrix to denote if there are edges between nodes. A is determined by the centerline structure and Z is the output of the graph convolutional neural network. It can be understood that other common methods used in CNN may also be used in graph convolutional neural network, such as skipping connection or attention, etc., which are not specifically limited in this disclosure.

As another example, graph-gated neural networks such as GRU or LSTM can also be used in the propagation step to improve the long-term propagation of information in the graph structure. For example, if the edges of the graph are directional, by using a gate mechanism, the parent node can selectively incorporate information from each child node. More concretely, each graph unit (could be a GRU or LSTM unit) contains input and output gates, a memory cell, and a hidden state. Instead of a single forget gate, each graph unit contains one forget gate for each child. The message passing could be bottom-to-up or up-to-bottom or both directions. It can be understood that the graph unit could be any RNN unit such as LSTM, GRU, CLSTM, CGRU, etc., which is not specifically limited in this disclosure.

In some embodiments, the anatomical structures include vascular structures or airway structures. The method provided by this disclosure may predict the disease quantification parameters of this anatomical tree structure based on the embed feature formed by the local feature and global feature of the vascular structure or airway structure together with the GNN. It may realize seamless integration the information from the sampling points in the centerline structure of the entire anatomical structure, and by taking both the local and global consideration factors of the sampling points into account, so that disease quantification parameters of the anatomical tree structure may be predicted accurately even with limited label data (for example, only a few ground truth values are available in the tree/graph structure).

Figure 3:
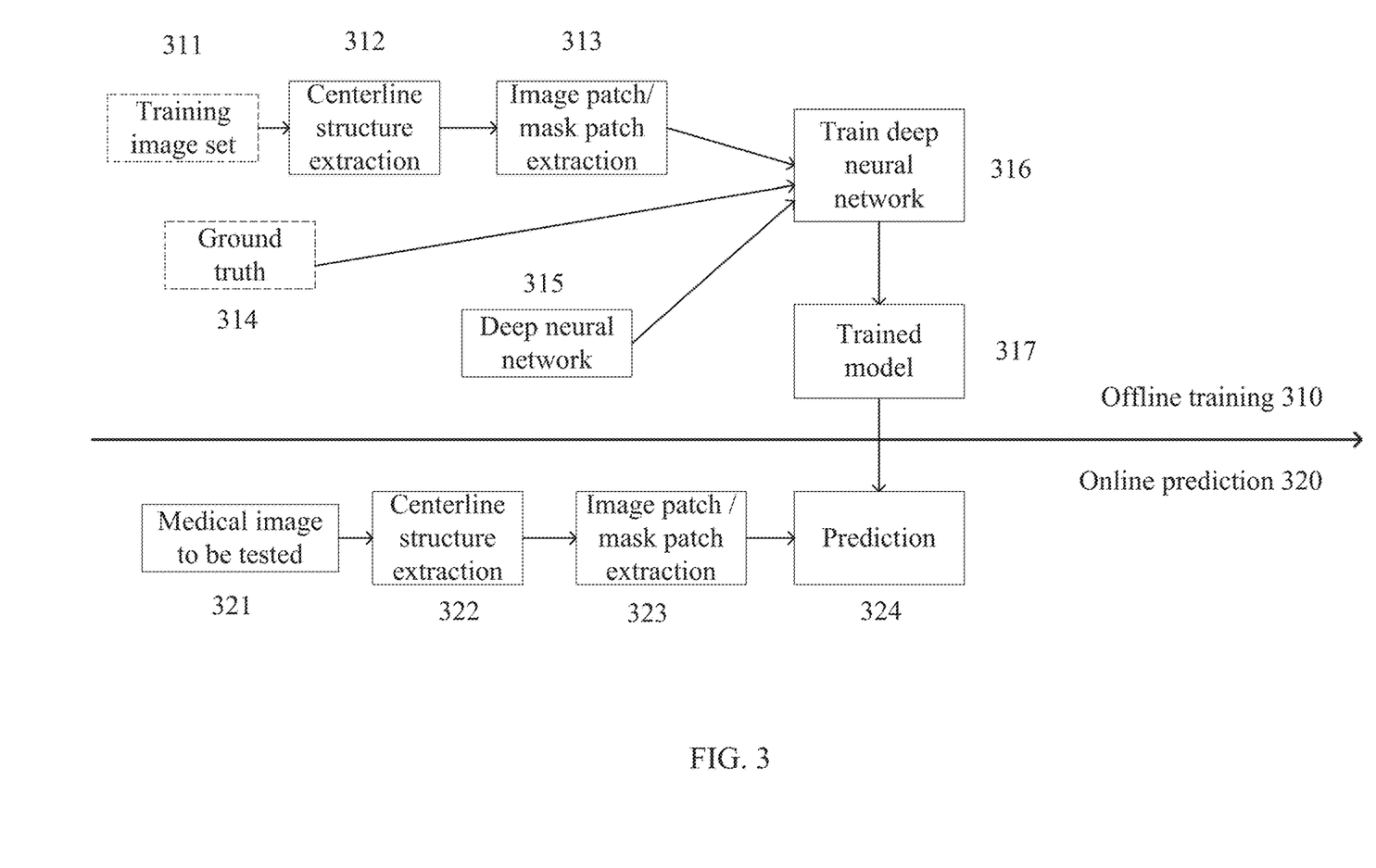
FIG. 3 shows a framework implemented by an exemplary method for training a Graph neural network and predicting disease quantitative parameters for an anatomical structure using Graph neural network, according to an embodiment of this disclosure.

FIG. 3 shows the framework of training a graph neural network and using it for disease quantification parameter prediction for an anatomical structure, according to an embodiment of this disclosure, including two stages, the offline training 310 and the online prediction 320. As shown in FIG. 3, during offline training 310, centerline structure extraction 312 is performed on the training samples in the training image set 311. A graph representation algorithm may be employed to create a graph structure representation for each training sample, and then image patch/mask patch extraction 313 may be performed on the extracted centerline structure obtained by the centerline structure extraction 312. The deep neural network 316 is trained by using the ground truth 314, the established deep neural network 315, and the image patch/mask patch obtained by the image patch/mask patch extraction 313, resulting in a trained model 317. During offline training, a database of training data annotated with ground truth may, be assembled, and the constructed deep neural network can learn to transmit information (message passing) between nodes with ground truth and nodes without ground truth through training.

In some embodiments, gradient-based methods (e.g., stochastic gradient descent, SGD) may be used for training to optimize the objective function for all parameters over the training dataset.

For example, for regression prediction problems with parameters such as FFR, the parameters of a regression graph neural network may be optimized by minimizing any regression loss function for the regression task. For example, the regression loss function may include the mean squared error (L2 loss) between the ground truth output y and the predicted value ŷ). Specifically, for the training set D, the parameters (θ) of the neural network are optimized to minimize the objective function J, as shown in equation (1) below:

$$J(\theta) = \frac{1}{D}\sum_{k=1}^{D} \|y - \hat{y}\|_2 \qquad \text{equation (1)}$$

As another example, for the classification prediction problem of patch stability level, the parameters of the classification graph neural network may be optimized by minimizing any classification loss function of the classification task. For example, this classification loss function may include the cross-entropy loss CE between the ground truth output y and the predicted value ŷ. In particular, for the training set D, the parameters (φ) of the classification graph neural network are optimized to minimize the objective function H, as shown in Equation (2) below:

$$H(\varphi) = \frac{1}{D}\sum_{k=1}^{D} CE(y - \hat{y}) \qquad \text{equation (2)}$$

During the online prediction 320, the trained model 317 from the offline training 310 may be used to predict the disease quantification parameters for an anatomical structure. Particularly, as shown in the online prediction 320 in FIG. 3, the centerline structure extraction 322 is performed on the medical image to be tested 321, and then image/mask patch extraction 323 is performed. The extracted image/mask patch may be input into the trained model 317 from the offline training 310 for prediction (prediction 324 shown in FIG. 3), thereby obtaining forecast result.

The prediction stage as shown in FIG. 1 may be completed in online prediction 320, so that disease quantification parameters FFR) for an anatomical structure of unseen data may be calculated by using the learned model from the offline training 310 stage.

By arranging the training process of a time-consuming and computationally heavy learning model to be performed offline, a computationally efficient deep learning model can be trained for a specific patient and/or doctor according to the needs. When predicting the disease status, the off-the-shelf trained learning model may be directly used for prediction, which takes less time and can meet the clinical needs.

Figure 4:
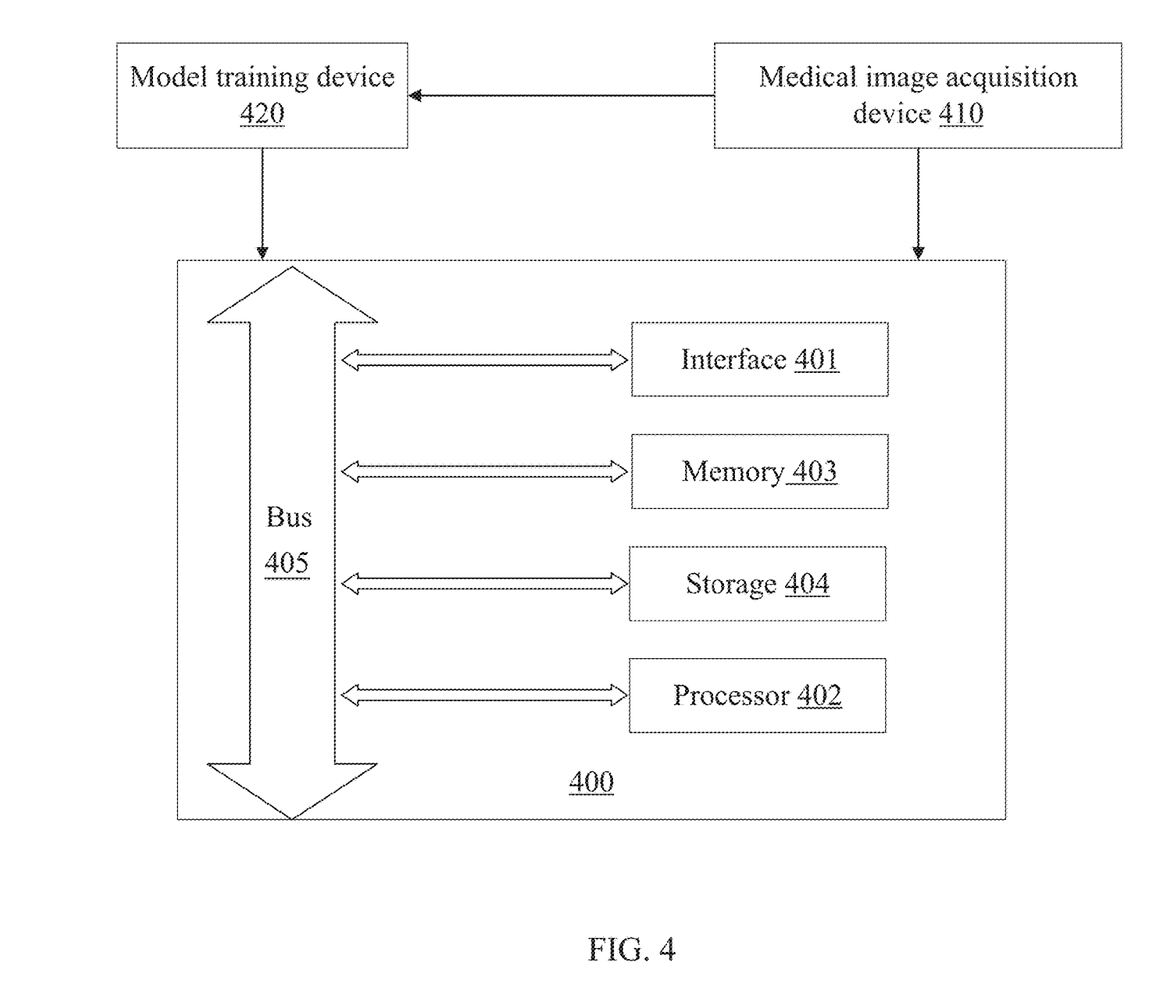
FIG. 4 illustrates a schematic diagram of a system for predicting disease quantification parameters for an anatomical structure, according to an embodiment of this disclosure.

This disclosure also provides a device for predicting disease quantification parameters for an anatomical structure. FIG. 4 shows a schematic diagram of a system for predicting disease quantification parameters for an anatomical structure according to an embodiment of this disclosure. As shown in FIG. 4, the system 400 may include an interface 401, which is configured to receive clinical data to be analyzed, and a processor 402, which is configured to perform a method of predicting disease quantification parameters for an anatomical structure according to various embodiments of this disclosure.

Particularly, as shown in FIG. 4, the interface 401 may receive the clinical data to be analyzed sent by the external medical image acquisition device 410, and send the medical image containing the anatomical structure to be analyzed to the processor 402, which may then apply the trained GNN to predict disease quantification parameters for the anatomical structure. The model training device 420 is used to construct a GNN, and receives sets of training data (e.g., from the medical image acquisition device 410 or training database) to train the constructed. GNN and send the trained GNN to the system 400. In this manner, the system 400 may apply the trained GNN to predict the disease quantification parameters for the anatomical structure when receiving the medical image containing the anatomical structure to be analyzed sent by the medical image acquisition device 410.

In some embodiments, the model training device 420 may additionally include input and output interfaces to communicate with the training database, network, and/or user interface. The user interface may be used for selecting sets of training data, adjusting one or more parameters of the training process, selecting or modifying a framework of the learning model, and/or manually or semi-automatically providing prediction results associated with a sequence of images for training.

In some embodiments, the obtained feature information together with the prediction result may also be stored in the model training device 420 as a new training sample, so as to continuously update the sets of training data and continuously improve the performance of the trained learning network. In addition, the stored parameters of the previously trained prediction model may be adopted as the initial parameters of the prediction model during post-training, which may greatly speed up the training process.

In some embodiments, as shown in FIG. 4, the system 400 may further include a memory 403, a storage 404 and a bus 405, and the interface 401, the memory 403, the storage 404, and the processor 402 are all connected with the bus 405 and communicate with each other through the bus 405.

It can be understood That the memory 403 may have the trained learning model and data stored thereon, such as feature information generated when the computer program is executed, etc. In some embodiments, storage 404 may store computer-executable instructions, such as one or more data processing programs. The computer-executable instructions may be loaded into memory 403 for execution by processor

402, In some embodiments, feature information may be extracted at different granularities from data slices stored in memory 403. In some embodiments, feature information may be read from memory 403 one by one or simultaneously and stored in storage 404. The processor 402 may be communicatively associated with the storage 404 and configured to execute computer-executable instructions stored thereon. The processor 402 may be configured to implement the various steps of the method for predicting disease quantification parameters for an anatomical structure according to various embodiments of the present disclosure, or the steps of the training process of training a predictive learning network such as GNN, by means of executing computer-executable instructions stored in the storage 404 or the memory 403.

In some embodiments, the GNNs of this disclosure may be stored in storage 404, Alternatively, the learning network may be stored in a remote device, a separate database, or a distributed device, and used by the data processing program(s).

In some embodiments, the model training device 420, the medical image acquisition device 410, and the system 400 may be provided within the same computer or processing device.

In some embodiments, interface 401 may include, but is not limited to, network adapters, cable connectors, serial connectors, USB connectors, parallel connectors, high-speed data transfer adapters, etc., such as fiber, USB 3.0, thunderbolt etc., wireless network adapters, such as WiFi adapters, telecommunication (3G, 4G/LTE, etc.) adapters, etc.

In some embodiments, the interface 401 may be a network interface, and the system 400 may be connected to a network through the interface 401, such as but not limited to a local area network or the Internet in a hospital. The network may connect the system 400 with external devices such as the medical image acquisition device 410, clinical databases, and clinical data storage devices (not shown). The medical image acquisition device 410 may also be any type of imaging modality such as, but not limited to, computed tomography (CT), digital subtraction angiography (DSA), magnetic resonance image (MRI), functional MRI, dynamic contrast enhancement—MRI, diffusion MRI, Spiral CT, Cone Beam Computed Tomography (CBCT), Positron Emission Tomography (PET), Single-Photon Emission Computed Tomography (SPECT), X-ray Imaging, optical tomography, fluorescence imaging, ultrasound imaging, radiotherapy portal imaging, etc.

In some embodiments, system 400 may be a dedicated smart device or a general-purpose smart device. For example, system 400 may be a computer customized for clinical data acquisition and clinical data processing tasks, or a server placed in the cloud. For example, system 400 may be integrated into medical image acquisition device 410.

In some embodiments, processor 402 may be a processing device that includes one or more general processing devices, such as a microprocessor, central processing unit (CPU), graphics processing unit (GPU), etc. processing equipment. More specifically, the processor 402 may be a complex instruction set arithmetic (CISC) microprocessor, a reduced instruction set computing (RISC) microprocessor, a very long instruction word (VLIW) microprocessor, a processor running other instruction sets, or a processor that runs a combination of instruction sets. The processor 402 may also be one or more dedicated processing devices such as an application specific integrated circuit (ASIC), a field programmable gate array (FPGA), a digital signal processor (DSP), a system-on-chip (SoC), or the like.

In some embodiments, processor 402 may be a dedicated processor rather than a general processor. The processor 402 may include one or more known processing devices, such as microprocessors from the Pentium™, Core™, Xeon™ or Itanium series manufactured by Intel™, and the like. The disclosed embodiments are not limited to any type of processor 402 or processor circuit that is otherwise configured to meet the needs of identifying, analyzing, maintaining, generating and/or providing large amounts of clinical data or manipulating such clinical data to provide computing requirements for disease condition prediction, or computing requirements for manipulating any other type of data consistent with the disclosed embodiments. Additionally, processor 402 may include one processor or more, e.g., a multi-core design or multiple processors, each processor having a multi-core design.

In some embodiments, storage 404 may store one or more software applications. Software applications stored in storage 404 may include, for example, operating systems (not shown) for common computer systems and operating systems for software controls. Furthermore, storage 404 may store the entire software application or only a portion of the software application executable by processor 402. In addition, storage 404 may store a number of software modules for implementing various steps of a method of predicting disease quantification parameters for an anatomy structure or a process for training a GNN consistent with the present disclosure.

In some embodiments, storage 404 may also store data generated/buffered during execution of computer programs, e.g., clinical data, including clinical data sent from (one or more) medical image acquisition device(s) 410, medical image databases, image data storage devices, etc. In some embodiments, storage 404 may be a non-transitory computer-readable medium, such as a read-only memory (ROM), a random access memory (RAM), a phase-change random access memory (PRAM), a static random access memory (SRAM)), a dynamic random access memory (DRAM), an electrically erasable programmable read-only memory (EEPROM), other types of random access memory (RAM), a flash disk or other forms of flash memory, a cache, a registers, a static memory, a compact disc read-only memory (CD-ROM), a digital versatile disc (DVD) or other optical storage, a cassette tape or other magnetic storage device, or any other non-transitory medium that may be used to store information or instructions capable of being accessed by a computer device, etc.

In some embodiments, the model training device 420 may be implemented in hardware specially programmed by software that performs the training phase. For example, the model training device 420 may include a processor and a non-transitory computer readable medium, and the processor 402 may implement the training by executing instructions of the training process stored in the computer readable medium.

The system 400 for predicting disease quantification parameters for an anatomical structure provided by this disclosure extracts the local feature of the sampling point of the centerline, and extracts the global feature based on a set of sampling points, and utilizes both the local feature and the global feature to obtain the embed feature for input into (the corresponding node of the) GNN, enabling seamless integration of information from sampled points of centerline structures on the anatomy structure by incorporating both local and global consideration factors of sampled points into the GNN, enabling accurate prediction of disease quantification parameters for an anatomical structure using only limited label data.

This disclosure also provides a computer-readable storage medium on which computer-executable instructions are stored. When the computer-executable instructions are executed by a processor, it may implement the method of prediction disease quantification parameters for an anatomical structure according to various embodiments of this disclosure.

Understandably, the computer-readable storage medium such as but not limited to a read-only memory (ROM), a random access memory (RAM), a phase-change random access memory (PRAM), a static random access memory (SRAM)), a dynamic random access memory (DRAM), an electrically erasable programmable read-only memory (EEPROM), other types of random access memory (RAM), a flash disk or other forms of flash memory, a cache, a registers, a static memory, a compact disc read-only memory (CD-ROM), a digital versatile disc (DVD) or other optical storage, a cassette tape or other magnetic storage device, or any other non-transitory medium that may be used to store information or instructions capable of being accessed by a computer device, etc.

Various operations or functions are described herein, which may be implemented or defined as software code or instructions. Such content may be directly executable ("object" or "executable" form) source code or differential code ("delta" or "patch" code). Software implementations of the embodiments described herein may be provided via an article of manufacture having code or instructions stored therein or via a method of operating a communications interface to transmit data via the communications interface. A machine or computer-readable storage medium can cause a machine to perform the functions or operations described, and includes any mechanism for storing information in a form accessible by a machine computing device, electronic system; etc.), such as recordable/non-recordable media (e.g., a read-only memory (ROM), a random access memory (RAM), a magnetic disk storage media, an optical storage media, flash memory devices, etc.). A communication interface includes any mechanism coupled to any one of hardwired, wireless, optical, etc., media to communicate with another device, such as a memory bus interface, a processor bus interface, an internet connection, a disk controller, and the like. The communication interface may be configured to prepare the communication interface to provide data signals describing the content of the software by providing configuration parameters and/or sending signals. The communication interface may be accessed via one or more commands or signals sent to the communication interface.

This disclosure also relates to a system for performing the operations herein. This system may be specially constructed for performing the specific methods disclosed herein, or the system may include a general computer selectively activated or reconfigured by a computer program stored in the computer. Such a computer program may be stored in a computer-readable storage medium such as, but not limited to, any type of disk such as a floppy disk, a compact disk, CDROM, a magneto-optical disk, a read-only memory (ROM), a random access memory (RAM). EPROM, EEPROM, magnetic or optical cards, or any type of medium suitable for storing electronic instructions, each of which is coupled to a computer system bus.

The above embodiments are only exemplary; and are not intended to limit the present invention, and the protection scope of the present invention is defined by the claims.

Those skilled in the art can make various modifications or equivalent replacements to the present invention within the spirit and protection scope of the present invention, and such modifications or equivalent replacements should also be regarded as falling within the protection scope of the present invention.

What is claimed is:

1. A computer-implemented method of predicting disease quantification parameters for an anatomical structure, comprising:
    receiving a medical image containing the anatomical structure;
    extracting, by at least one processor, a centerline structure based on the medical image; and
    predicting the disease quantification parameter for each sampling point the extracted centerline structure by using a graph neural network (GNN), wherein each node of the GNN corresponds to a sampling point on the extracted centerline structure and each edge of the GNN corresponds to a spatial constraint relationship between two sampling points, wherein predicting the disease quantification parameter for each sampling point further comprises:
        extracting a local feature based on an image patch for the sampling point by using a local feature encoder;
        extracting a global feature by using a global feature encoder based on a set of image patches for a set of sampling points, which include the sampling point and have a spatial constraint relationship defined by the centerline structure; and
        obtaining an embed feature based on both the local feature and the global feature and inputting the embed feature to the node of the GNN corresponding to the sampling point.

2. The computer-implemented method of claim 1, wherein each of the local feature encoder and the global feature encoder adopts a dual-level attention mechanism comprising a first level attention module and a second level attention module, wherein the first level attention module is configured to extract a diseased location-aware attention map and the second level attention module is configured to extract a pixel-to-pixel inter-dependence attention map.

3. The computer-implemented method of claim 1, wherein the GNN includes a high-order GNN.

4. The computer-implemented method of claim 1, wherein the anatomical structure includes an anatomical tree structure or an anatomical graph structure.

5. The computer-implemented method of claim 1, wherein the local feature encoder includes a first CNN combined with an attention mechanism for localization, followed by a first self-attention block combined with an attention mechanism for pixel-to-pixel correlation.

6. The computer-implemented method of claim 1, wherein the global feature encoder includes a second CNN combined with an attention mechanism for localization, followed by a RNN, which is then followed by a second self-attention block combined with an attention mechanism for pixel-to-pixel correlation, wherein the RNN is configured to accumulate information from a root of the anatomical structure to the current sampling point.

7. The computer-implemented method of claim 5, wherein the attention mechanism for localization includes a residual attention, and the first self-attention block includes a nonlocal network.

8. The computer-implemented method of claim 1, wherein obtaining an embed feature based on both the local feature and the global feature further comprises concatenating the local feature and the global feature to obtain the embed feature.

9. The computer-implemented method of claim 1, wherein the GNN includes a graph convolution based neural network or a graph gated based neural network.

10. The computer-implemented method of claim 1, wherein the anatomical structure includes a vessel structure or an airway structure.

11. A system for predicting disease quantification parameters for an anatomical structure, which comprises:
    an interface configured to receive a medical image containing the anatomical structure; and
    a processor configured to:
        extract a centerline structure based on the medical image; and
        predict the disease quantification parameter for each sampling point on the extracted centerline structure by using a graph neural network (GNN), wherein each node of the GNN corresponds to a sampling point on the extracted centerline structure and each edge of the GNN corresponds to a spatial constraint relationship between two sampling points, wherein to predict the disease quantification parameter for each sampling point, the processor is further configured to:
        extract a local feature based on an image patch for the sampling point by using a local feature encoder;
        extract a global feature by using a global feature encoder based on a set of image patches for a set of sampling points, which include the sampling point and have a spatial constraint relationship defined by the centerline structure; and
        obtain an embed feature based on both the local feature and the global feature and inputting the embed feature to the node of the GNN corresponding to the sampling point.

12. The system of claim 11, wherein each of the local feature encoder and the global feature encoder adopts a dual-level attention mechanism comprising a first level attention module and a second level attention module, wherein the first level attention module is configured to extract diseased location-aware attention map and the second level attention module is configured to extract pixel-to-pixel inter-dependence attention map.

13. The system of claim 11, wherein the GNN includes a high-order GNN.

14. The system of claim 11, wherein the anatomical structure includes an anatomical tree structure or an anatomical graph structure.

15. The system of claim 11, wherein the local feature encoder includes a first CNN combined with an attention mechanism for localization, followed by a first self-attention block combined with an attention mechanism for pixel-to-pixel correlation.

16. The system of claim 11, wherein the global feature encoder includes a second CNN combined with an attention mechanism for localization, followed by a RNN, which is then followed by a second self-attention block combined with an attention mechanism for pixel-to-pixel correlation, wherein the RNN is configured to accumulate the information from a root of the anatomical structure to the current sampling point.

17. The system of claim 11, wherein to obtain an embed feature based on both the local feature and the global feature, the processor is further configured to concatenate the local feature and the global feature to obtain the embed feature.

18. The system of claim 11, wherein the GNN includes a graph convolution based neural network or a graph gated based neural network.

19. The system of claim 11, wherein the anatomical structure includes a vessel structure or an airway structure.

20. A non-transitory computer-readable storage medium, with computer executable instructions stored thereon, which, when being performed by a processor, perform a method of predicting disease quantification parameters for an anatomical structure, the method comprising:
    receiving a medical image containing the anatomical structure;
    extracting a centerline structure based on the medical image; and
    predicting the disease quantification parameter for each sampling point on the extracted centerline structure by using a graph neural network (GNN) where each node of the GNN corresponds to a sampling point on the extracted centerline structure and each edge of the GNN corresponds to a spatial constraint relationship between two sampling points, wherein predicting the disease quantification parameter for each sampling point further comprises:
    extracting a local feature based on an image patch for the sampling point by using a local feature encoder;
    extracting a global feature by using a global feature encoder based on a set of image patches for a set of sampling points, which include the sampling point and have a spatial constraint relationship defined by the centerline structure; and
    obtaining an embed feature based on both the local feature and the global feature and inputting the embed feature to the node of the GNN corresponding to the sampling point.

* * * * *